United States Patent [19]

McNew et al.

[11] 4,438,593

[45] Mar. 27, 1984

[54] ANTI-FUNGAL PERFORMANCE IN PELLETED SEEDS THROUGH USE OF HYDROPHOBES

[75] Inventors: George L. McNew, Hastings on the Hudson, N.Y.; Norman W. Thomas, Warren, N.J.

[73] Assignee: Celanese Corporation, New York, N.Y.

[21] Appl. No.: 1,735

[22] Filed: Jan. 8, 1979

Related U.S. Application Data

[63] Continuation of Ser. No. 782,645, Mar. 30, 1977, abandoned.

[51] Int. Cl.[3] .................... A01C 1/06; A01N 43/36; A01N 47/28; A01N 61/00

[52] U.S. Cl. .................................. 47/57.6; 424/80; 424/167; 424/273 B; 424/274; 424/322; 424/349

[58] Field of Search .................... 424/274, 273 B, 322, 424/167, 349, 80; 47/57.6

[56] References Cited

U.S. PATENT DOCUMENTS 3,849,934  11/1974  Dorschner et al. .................. 47/57.6

*Primary Examiner*—Allen J. Robinson
*Attorney, Agent, or Firm*—Scully, Scott, Murphy & Presser

[57] ABSTRACT

The addition of a particulate non-phytotoxic hydrophobe to the coating of pelleted seed substantially improves the effectiveness of the anti-fungal agent present on the seed surface or contained in the coating composition against soil-borne phytopathogenic fungi.

22 Claims, No Drawings

ANTI-FUNGAL PERFORMANCE IN PELLETED SEEDS THROUGH USE OF HYDROPHOBES

This is a continuation of application Ser. No. 782,645, filed Mar. 30, 1977, now abandoned.

BACKGROUND OF THE INVENTION

1. Field of the Invention

This invention relates to pelleted seed and to processes for their production, and more particularly, to pelleted seed having enhanced protection from soil-borne phytopathogenic fungi.

2. Description of the Prior Art

For some years, it has been of considerable interest to mechanize or automate the planting and cultivating of seeds so that increased production and lower labor costs may be realized, especially in large scale agricultural, horticultural and reforestation operations. Mechanical planters are now in use which efficiently and precisely place single seeds into soil at a predetermined depth and interval (which may vary according to seed type) thereby reducing the need for such subsequent labor-intensive procedures as thinning. While the use of mechanical planters has become widely accepted for planting seeds of relatively large and regular shape, e.g., corn and the like, many vegetable seeds in the natural state are ill-suited for mechanized planting due to their physical form. The small size and/or irregular shape of lettuce, sugarbeet, celery and other seeds tends to cause jamming and packing of the feeding component of mechanical planters currently in use. Heretofore, it has been a practice to adapt these seeds for mechanical planting by coating them with a composition which increases their dimensions and/or smooths their surface. In order to improve the viability of the seeds, anti-fungal agents have been incorporated into the coating composition to protect the seeds from phytopathogenic fungi present in the soil during the germination and emergence periods. To the extent such anti-fungal agents fail to perform, it becomes necessary to plant an excess of seed if a satisfactory crop yield is to be obtained from a given area of land. Overplanting will require that the young crop be thinned back to an optimum population. Thinning is an expensive hand labor operation and reduces the economies to be gained by mechanized planting. Accordingly, it is highly desirable that the viability of coated seed be maintained at as close a level to maximum as possible so as to avoid or reduce the necessity of overplanting and subsequent thinning.

Illustrative of known coated seeds which may contain a biocide as a component of their coating compositions are those described in U.S. Pat. Nos. 2,651,883; 3,545,129; 3,598,565; 3,698,133; and 3,905,152. However, in none of the coating compositions of the foregoing patents is there suggested the combination of a non-phytotoxic hydrophobe and an anti-fungal agent specific in its activity against soil-borne phytopathogenic fungi.

SUMMARY OF THE INVENTION

It has been very surprisingly discovered that the addition of at least one particulate non-phytotoxic hydrophobe to a seed coating composition greatly potentiates, for reasons yet unknown, the effectiveness of an anti-fungal agent (specifically active against soil borne phytopathogenic fungi) present on the seed surface or contained in the coating composition with a subsequent marked increase in seed germination and emergence rates.

Broadly stated, the pelleted seeds of this invention possess a continuous, adherent coating composition thereon comprising:

(a) an anti-fungally effective, but non-phytotoxic, amount of an anti-fungal agent specifically effective against soil-borne phytopathogenic fungi, the agent being present at the interface of the seed surface and the coating composition or within the interior of the coating composition;

(b) a particulate non-phytotoxic hydrophobe present in an amount sufficient to potentiate the effectiveness of the anti-fungal agent; and (c) a non-phytotoxic binder present in an amount at least sufficient to maintain the mechanical integrity of the coating until the pelleted seeds are planted.

The much enhanced viability of seeds coated in accordance with this invention as more fully described hereinafter greatly reduces, if not eliminates, the need for overplanting and such subsequent post-planting field operations as thinning.

DESCRIPTION OF THE PREFERRED EMBODIMENTS

The anti-fungal agents which can be selected for use herein must be specifically active against one or more soil-borne phytopathogenic fungi in contrast to those anti-fungal agents such as many of the mercury-containing biocides which are at most only marginally effective against these microorganisms (United States Department of Agriculture Yearbook for 1961, p. 276). Examples of soil-borne fungi which are pathogenic to seeds and seedlings are various species of such genera; Rhizoctonia, Thielaviopsis, Phythium, Fusarium, Sclerotium, Aphanomyces, Urocystis, Pyrenochaeta, Glomerella, Helminthosporium, Rhizopus, Aspergillus, Phoma, Ustilago, and the like. Among the many known and conventional anti-fungal agents which are effective against one or more of the foregoing soil fungi species and which can be advantageously employed in the seed coating compositions of this invention are included ORTHOCIDE (Captan; N-trichloromethylmercaptotetrahydrophthalimide), any of the alpha-aryl-N-lower alkyl nitrones described in U.S. Pat. No. 3,849,934 which is incorporated by reference herein, and 2-furyl-benzimidazole. The amount of anti-fungal agent to be applied to the seed surface or in the seed coating compositions herein will vary according to the phytopathogenic nature of the soil and the susceptibility of a particular seed to fungal attack, but in any event, will be within the level of tolerance of the seed. In general, from about 0.1 to 5% of anti-fungal agent by weight of coating composition will provide a satisfactory level of protection. The fungicide, if a powder, can be applied to the seed surface or distributed uniformly or in concentrated layers within the coating composition. Liquid fungicide can be applied to the seeds, generally by soaking the seeds in a dilute solvent solution of fungicide or can be added to the coating compositions in a manner similar to powder.

The term "hydrophobe" as used herein relates to substances which are not wetted to any appreciable extent by water. Among the particulate non-phytotoxic hydrophobes which can advantageously be used herein are included SILANOX, a colloidal silica which has been chemically modified to contain trimethyl silyl groups, polyolefins such as polyethylene and polypropylene, polyhalo-olefins, polystyrenes, polyvinyls, vinylidene polymers, polydienes, natural and synthetic waxes, rubbers, silanized materials, fluoropolymers, fluorocarbon-treated materials, and the like.

Any of the known and conventional non-phytotoxic binders heretofore employed in seed coating compositions can be effectively utilized herein. Preferably, the binders are of the water soluble type although it will be understood that emulsion type binders, for example, latices of polyvinyl acetate can also be used herein with acceptable results. Included amongst the water soluble binders, in a suitable solvent carrier, e.g., water or alcohol, are GELVATOL, a polyvinyl alcohol resin of about 3,000 average molecular weight, 37–42 weight percent residual acetate content and 73–77 weight percent hydrolysis, polyvinylpyrrollidone, methyl cellulose, hydroxypropyl cellulose, cellulose acetate, dextrins, sugar, molasses, karaya gum, jaguar gum, tragacanth gum, polysaccharide gum, natural glue, mucilage and like substances affording adhesiveness.

Any of the known and conventional inert particulate fillers heretofore employed in the coating of seeds can advantageously be utilized herein. Included amongst such fillers are PYRAX, a ground pyrophyllite-aluminum silicate, clay, powdered silica, diatomaceous earth, flyash, chalk, ground limestone, sandy loam, talc, powdered charcoal, gypsum, powdered feldspar, powdered vermiculite, kaolin, ground peat moss, and the like.

It is also within the scope of this invention to include in the coating composition herein conventional germination enhancing materials, fertilizers, growth regulants, inoculants such as bacterial cultures, nutrients, and other similar materials. These materials can be applied directly to the seed surface, they can be part of the coating composition, or they can be applied to the surface of the pelleted seed upon completion of the coating process.

The size of the hydrophobe particles and optional filler particles used to form the seed coating can vary within wide limits depending upon the type of seed to be coated. It is generally advantageous for the particles to be smaller than the seed so as to provide satisfactory buildup of the coating around the seed. To coat common vegetable seeds such as lettuce, sugar beet, radish, onion, celery, cucumber, carrot, spinach, tomato, cabbage, and the like, which seeds generally range in size from about 1 to 10 mm at their largest dimension, spherical, spheriodal or irregularly-shaped particles in the size range of about 5 millimicron to about 900 microns can be used. It is preferred to use fine spheroidal particles in the size range of up to about 250 microns. When extremely small seeds, such as many of the flower seeds, are to be coated, it is advantageous to begin the coating operation with small particles and complete the coating with larger particles.

The relative proportions of hydrophobe, binder and optionally, filler, can also vary within wide limits depending upon the nature of the coating materials selected, the seed type, the nature of the soil, the character of the fungal infestation and the planting season as will be readily appreciated by those skilled in the art. Generally, the hydrophobe must be present in an amount of at least about 0.1% by weight of the total coating composition to improve the effectiveness of the anti-fungal agent to an appreciable degree. Advantageously, the hydrophobe can represent from about 0.5% to about 30% of the weight of the coating composition for most seeds. SILANOX has been used with very good results at levels of about 0.1% to 1.0% by weight. The amount of binder, exclusive of carrier, should be as small as possible consistent with the mechanical integrity necessary for shipping, handling and planting the coated seed. The amount of a particular binder which is used will depend upon its adhesive properties and generally should not exceed about 10% of the coating composition by weight. Advantageously from about 3 to 5% binder can be utilized with good results. The amount of filler, if any, will represent the balance of the coating formulation.

The coatings are built up on the seeds employing known and conventional techniques such as pan-coating or spraying the binder dissolved in a liquid carrier such as water onto a mixture of the seed, particulate material and anti-fungal agent rotating in a mixer of conventional type. Another useful process is the Wurster Air Suspension Coating Process which is described in U.S. Pat. Nos. 2,799,241; 3,089,824; 3,177,027; 3,196,827; 3,207,824; 3,241,520; and 3,253,994. The coating thickness will be at least sufficient for the purpose of mechanized planting, i.e., about 3 mm. Advantageously, the concentration of hydrophobe in the mixture of coating materials can be adjusted toward the end of the coating operation to provide a greater amount of hydrophobe on the exterior surface of the seed coating where it has been found to be most effective. As mentioned hereinabove, the anti-fungal agent may be precoated upon the seed, or incorporated into the coating composition.

According to the results set forth in the following TABLE, lettuce seeds (Empire) coated in accordance with this invention, i.e., wherein the coating formulation contains both a non-phytotoxic hydrophobe (SILANOX) and an anti-fungal agent (Captan) specific against soil-borne fungi, in this case, the species Pythium, demonstrated a greatly improved rate of emergence compared to pelleted seeds lacking one or both of these materials. The amounts and nature of the binder, filler and hydrophobe components of the coating composition, and the procedure for applying the coating compositions to seed, were in all cases identical.

The seeds were coated with a composition comprising Gelvatol (polyvinyl alcohol resin of about 3000 average molecular weight, 73–77 percent hydrolyzed, comprising 37–42 weight percent residual acetate units) as binder, Pyrax (a ground pyrophyllite-aluminum silicate) as filler, Captan (N-trichloromethylmercaptotetrahydrophthalimide) as functional fungicide and Silanox as hydrophobe. The method of coating involved wetting the seeds by spraying with the Gelvatol (supplied as a 5% aqueous solution) component, pan coating with Pyrax to effect coating buildup to ensuing singulation, rewetting with Gelvatol solution, applying, again by pan coating, a prepared admixture of Captan and Pyrax to singulation, surface wetting with Gelvatol and dusting with Silanox. Coating buildup was effected to a total of 5 to 10 times the weight of raw seed.

The coating of a given seed ranged over 5 to 10 parts by weight of Pyrax, 0.001 to 0.002 parts of Captan, and 0.05 to 0.30 parts of Gelvatol and less than 0.5 percent of Silanox, all by weight of raw seed. In the above-described method and in the runs reported in the following Table, the coating was multilayered, i.e., the fungicide containing layer constituted an intermediate coat, with the inner coat including about ⅔ of the Pyrax and Gelvatol employed. The Silanox hydrophobic agent was surface dusted onto the exterior of the precoated seed, to form a regular essentially homogeneous distribution of hydrophobe sufficient to inhibit capillary formation with resultant intrusion of moisture. Under germination conditions, involving significant moisture levels, the coating composition essentially falls away from and is therefore efficiently divested by the seed.

TABLE

| Coating Compositions | | Captan oz./100 lbs. | SILANOX | %, Seed Emergence | | | |
|---|---|---|---|---|---|---|---|
| | | | | Sterile Soil | | Soil Infested with Pythium | |
| Binder | Filler | | | Wet | Dry | Wet | Dry |
| — | — | — | — | 96 | 93 | 33 | 68 |
| Yes | — | — | Yes | 97 | 93 | 48 | 46 |
| Yes | Yes | — | — | 93 | 89 | 27 | 61 |
| Yes | Yes | — | Yes | 95 | 88 | 37 | 66 |
| Yes | Yes | 3 | — | 90 | 96 | 34 | 88 |
| Yes | Yes | 3 | Yes | 95 | 94 | 80 | 86 |
| Yes | Yes | 2 | — | 89 | 96 | 48 | 93 |
| Yes | Yes | 2 | Yes | 98 | 96 | 83 | 90 |
| Yes | Yes | 1.5 | — | 93 | 97 | 34 | 96 |
| Yes | Yes | 1.5 | Yes | 100 | 93 | 91 | 93 |

What is claimed is:

1. A seed possessing a continuous, adherent coating composition thereon comprising:
   (a) an anti-fungal agent specifically effective against soil-borne phytopathogenic fungi in an amount of from about 0.1 to 5% by weight based on the weight of the coating composition;
   (b) a particulate non-phytotoxic hydrophobe present in an amount of about 0.5 to about 30% by weight based on the weight of the coating composition; and
   (c) a non-phytotoxic binder present in an amount at least sufficient to maintain the mechanical integrity of the coating until the pelleted seeds are planted.

2. The seed of claim 1 in which the anti-fungal agent is selected from the group consisting of N-trichloromethylmercaptotetrahydrophthalimide, an alpha-aryl-N-lower alkyl nitrone and 2-furyl-benzimidazole.

3. The seed of claim 1 in which the coating composition further contains an inert particulate filler.

4. The seed of claim 3 in which the inert particulate filler is selected from the group consisting of ground pyrophyllite-aluminum silicate, clay, powdered silica, diatomaceous earth, flyash, chalk, ground limestone, sandy loam, talc, powdered charcoal, gypsum, powdered feldspar, powdered vermiculite, kaolin and ground peat moss.

5. The seed of claim 1 in which the binder is water soluble.

6. The seed of claim 5 in which the water soluble binder is selected from the group consisting of polyvinyl alcohol, polyvinylpyrrolidone, methyl cellulose, cellulose acetate, dextrin, sugar, molasses, karaya gum, tragacanth gum, polysaccharide gum, natural glue and mucilage.

7. The seed of claim 6 in which the binder is present in an amount not exceeding about 10% by weight of the coating composition.

8. The seed of claim 1 in which the binder is an aqueous latex emulsion.

9. The seed of claim 8 in which the latex is polyvinyl acetate.

10. The seed of claim 3 in which the filler and the hydrophobe particles are smaller than the size of the seed to be coated.

11. The seed of claim 9 in which the filler and the hydrophobe particles are spherical and are within the size range of about 5 millimicrons to 250 microns.

12. A method of enhancing the viability of pelleted seed in a soil infested with phytopathogenic fungi which comprises coating the seed with a continuous, adherent coating composition comprising:
   (a) an anti-fungal agent specifically effective against soil-borne phytopathogenic fungi in an amount of from about 0.1 to 5% by weight based on the weight of the coating composition present at the interface of the seed surface and the coating composition or within the interior of the coating composition;
   (b) a particulate non-phytotoxic hydrophobe present in an amount of about 0.5 to about 30% by weight based on the weight of the coating composition; and
   (c) a non-phytotoxic binder present in an amount at least sufficient to maintain the mechanical integrity of the coating until the pelleted seeds are planted.

13. The method of claim 11 in which the anti-fungal agent is selected from the group consisting of N-trichloromethylmercaptotetrahydrophthalimide, an alpha-aryl-N-lower alkyl nitrone and 2-furyl-benzimidazole.

14. The method of claim 12 in which the coating composition further contains an inert particulate filler.

15. The method of claim 14 in which the inert particulate filler is selected from the group consisting of ground pyrophyllite-aluminum silicate, clay, powdered silica, diatomaceous earth, flyash, chalk, ground limestone, sandy loam, talc, powdered charcoal, gypsum, powdered feldspar, powdered vermiculite, kaolin and ground peat moss.

16. The method of claim 12 in which the binder is water soluble.

17. The method of claim 16 in which the water soluble binder is selected from the group consisting of polyvinyl alcohol, polyvinylpyrrolidone, methyl cellulose, cellulose acetate, dextrin, sugar, molasses, alginate, karaya gum, tragacanth gum, polysaccharide gum, natural glue and mucilage.

18. The method of claim 17 in which the binder is present in an amount not exceeding about 10% by weight of the coating composition.

19. The method of claim 12 in which the binder is an aqueous latex emulsion.

20. The method of claim 19 in which the latex is polyvinyl acetate.

21. The method of claim 14 in which the filler and the hydrophobe particles are smaller than the size of the seed to be coated.

22. The method of claim 21 in which the filler and the hydrophobe particles are spherical and are within the size range of about 5 millimicrons to 250 microns.

* * * * *

UNITED STATES PATENT AND TRADEMARK OFFICE
CERTIFICATE OF CORRECTION

PATENT NO. : 4,438,593
DATED : March 27, 1984
INVENTOR(S) : George L. McNew, Norman W. Thomas It is certified that error appears in the above-identified patent and that said Letters Patent is hereby corrected as shown below:

Column 4, line 20, "3,177,027" should be --3,117,027--.

Signed and Sealed this

Fifth Day of November 1985

[SEAL]

*Attest:*

*Attesting Officer*

DONALD J. QUIGG

*Commissioner of Patents and Trademarks*